United States Patent

Wozencroft

[11] Patent Number: 5,718,688
[45] Date of Patent: Feb. 17, 1998

[54] CATHETER PLACEMENT UNITS

[75] Inventor: Robert Michael Wozencroft, Surbiton, England

[73] Assignee: Sterimatic Holdings Limited, Tortola, Virgin Islands (Br.)

[21] Appl. No.: 516,829

[22] Filed: Aug. 18, 1995

[30] Foreign Application Priority Data

Aug. 24, 1994 [GB] United Kingdom ............... 9417073

[51] Int. Cl.$^6$ .................................................. A61M 5/178
[52] U.S. Cl. ........................................ 604/164; 604/165
[58] Field of Search ................................ 604/164, 110, 604/263, 198, 162, 166, 168, 165

[56] References Cited

U.S. PATENT DOCUMENTS

| 4,778,453 | 10/1988 | Lopez. | |
|---|---|---|---|
| 4,790,828 | 12/1988 | Dombrowski et al. | |
| 4,944,725 | 7/1990 | McDonald. | |
| 4,944,728 | 7/1990 | Carrell et al. | |
| 4,950,252 | 8/1990 | Luther et al. | |
| 4,978,344 | 12/1990 | Dombrowski et al. | |
| 4,994,042 | 2/1991 | Vadher. | |
| 5,007,901 | 4/1991 | Shields | 604/164 |
| 5,013,304 | 5/1991 | Russell et al. | 604/164 |
| 5,026,351 | 6/1991 | Dizon. | |
| 5,051,109 | 9/1991 | Simon. | |
| 5,102,394 | 4/1992 | Lasaitis et al. | 604/164 |
| 5,176,655 | 1/1993 | McCormick et al. | |
| 5,183,468 | 2/1993 | McLees. | |
| 5,186,712 | 2/1993 | Kelso et al. | 604/164 |
| 5,215,528 | 6/1993 | Purdy et al. | 604/164 |
| 5,279,591 | 1/1994 | Simon. | |
| 5,300,045 | 4/1994 | Plassche, Jr. | |
| 5,348,544 | 9/1994 | Sweeney et al. | |
| 5,533,974 | 7/1996 | Gaba | 604/164 |
| 5,584,809 | 12/1996 | Gaba | 604/110 |
| 5,599,310 | 2/1997 | Bogert | 604/164 |

FOREIGN PATENT DOCUMENTS

| WO 89/10767 | 11/1989 | WIPO. |
| WO 90/08564 | 8/1990 | WIPO. |
| WO 91/01151 | 2/1991 | WIPO. |
| WO 93/05840 | 4/1993 | WIPO. |

*Primary Examiner*—Mark Polutta
*Attorney, Agent, or Firm*—Young & Thompson

[57] ABSTRACT

A catheter placement unit comprises a catheter having an axial bore, a catheter hub at one end of the catheter, an introducing needle having a pointed tip for introducing the catheter into a desired position in a patient's body, and a needle hub on the needle remote from the tip for mounting the needle so that it extends through the catheter bore for introduction of the catheter into the patient's body and so that it can subsequently be withdrawn from the catheter bore leaving the catheter in position in the patient's body. The unit includes a needle tip protector on the needle for shielding the needle tip when the needle has been withdrawn from the catheter bore. The needle tip protector includes a locking device which is initially in an unlocked position permitting withdrawal of the needle from the catheter bore but which is arranged to be placed in a locked position, in which the locking device engages the outer surface of the needle, by withdrawal of the needle from the catheter bore so as to lock the needle tip protector on the needle in the shielding position. The locking device retains the catheter hub on the needle when the locking device is in the unlocked position and releases the catheter hub from the needle when the locking device is in the locked position. Separation of the catheter from the needle is therefore prevented until the needle has been withdrawn from the catheter bore to trigger shielding of the needle tip.

9 Claims, 2 Drawing Sheets

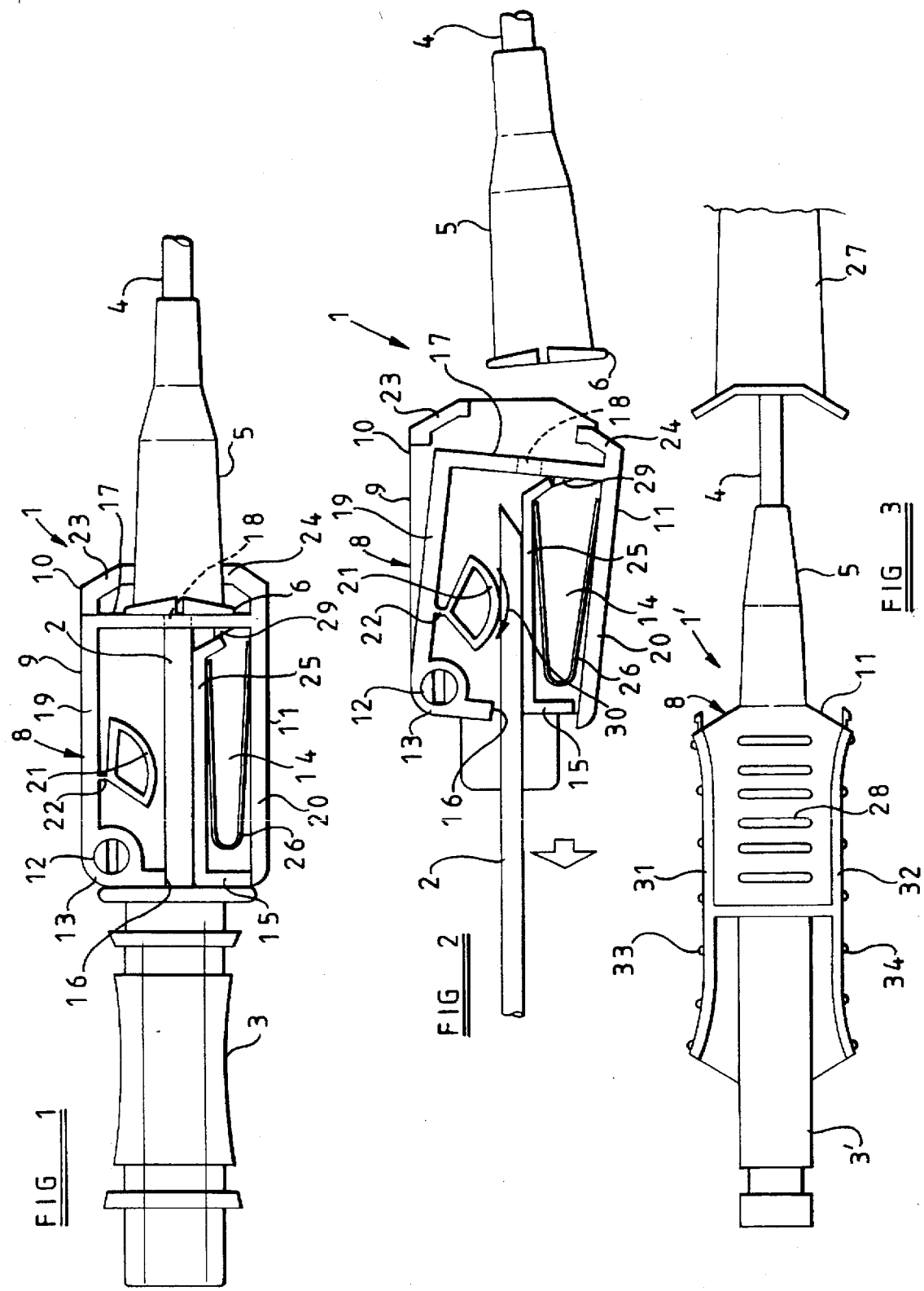

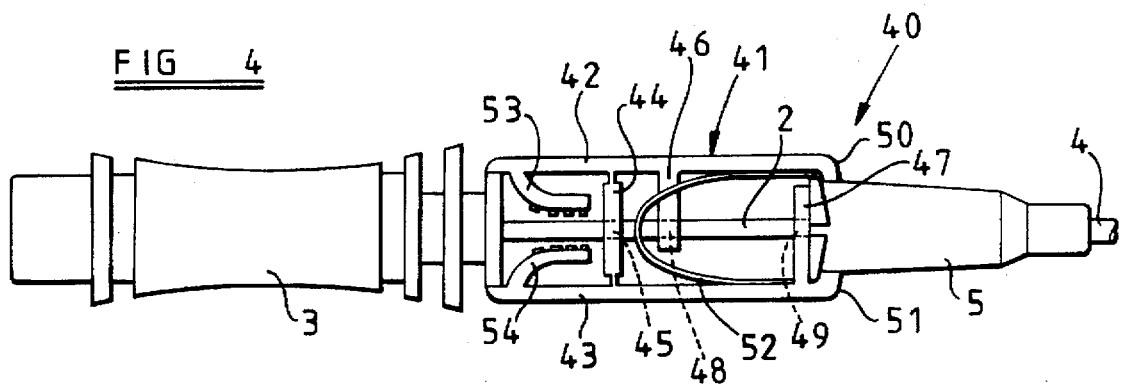
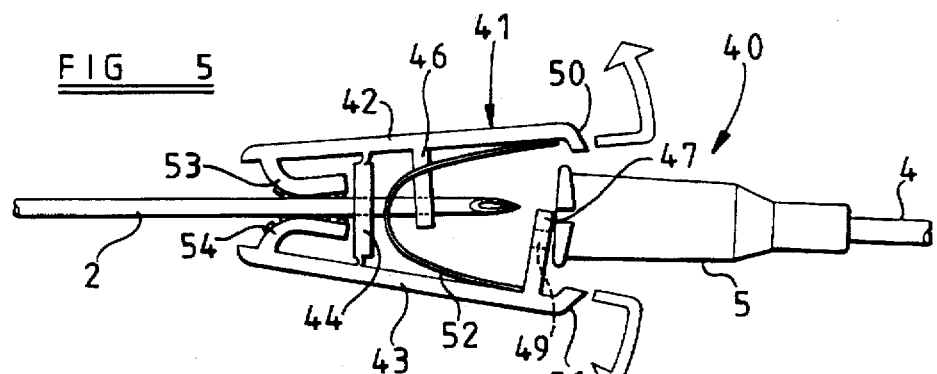
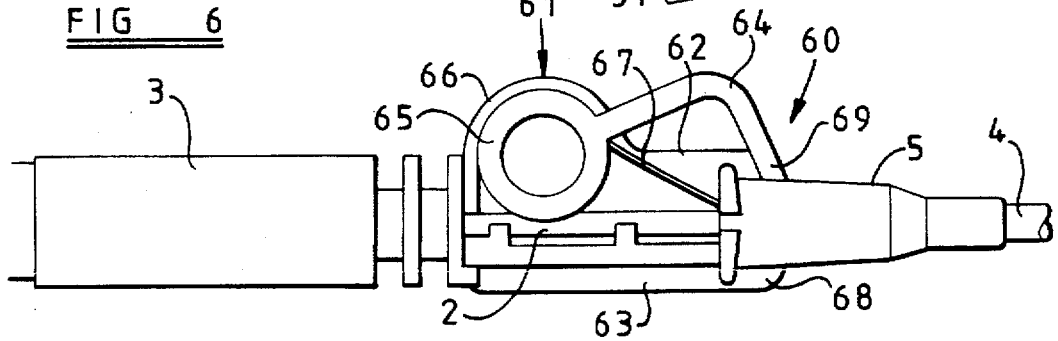
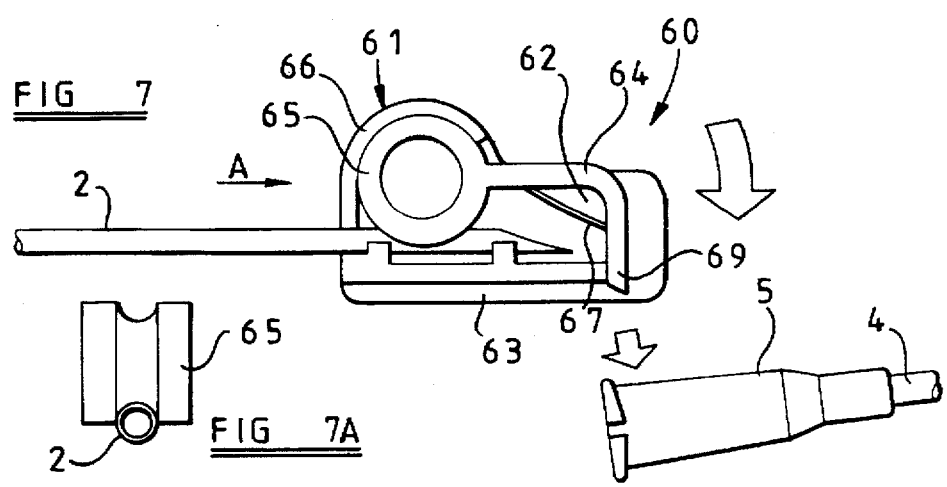

5,718,688

CATHETER PLACEMENT UNITS

BACKGROUND OF THE INVENTION

It is established medical practice to introduce a flexible tubular catheter into a desired position in a patient's body by means of a catheter placement unit which includes an introducing needle extending externally or internally of the catheter and projecting beyond the end of the catheter. In use of such a catheter placement unit to place a catheter within a patient's vein, for supply of infusion fluid for example, the needle tip projecting beyond the end of the catheter serves to puncture the patient's skin and to locate the catheter within the vein. When the catheter is suitably positioned, as may be determined by the flow of blood in the hub of the needle, the needle may be withdrawn leaving the catheter in position in the vein. However the need to withdraw the needle from the catheter leads to a risk that doctors or nurses will accidentally stick themselves with the needle, and this can be highly dangerous due to the risk of transfer of blood-related diseases.

WO 93/05840 discloses a catheter placement unit incorporating a needle tip protector which is mounted on the needle so that, on withdrawal of the needle from the catheter, the needle tip protector is caused to assume a shielding position in which it shields the needle tip, retention of the needle tip protector on the needle being ensured by a strap extending between the protector and the needle hub. However the provision of such a strap complicates production and assembly of the unit, as well as being inconvenient in use and limiting the needle tip protector to use with a needle of a length appropriate to the length of the strap.

WO 90/08564 discloses a needle tip protector which is retained in a position on the needle shielding the needle tip without requiring the provision of a strap extending between the protector and the needle hub. To this end the needle tip protector includes a locking device which is initially in an unlocked position permitting withdrawal of the needle from the catheter but which is arranged to be placed in a locked position by withdrawal of the needle from the catheter so as to lock the needle tip protector on the needle in its shielding position. However such a needle tip protector is complicated to produce and assemble, as well as suffering from the serious disadvantage that, since no special provision is made for release of the needle tip protector from the catheter hub on withdrawal of the needle, there is a danger that the catheter may be accidentally pulled off the needle leaving the needle tip unprotected or that the catheter may be accidentally withdrawn from the patient's vein during withdrawal of the needle.

Other catheter placement units incorporating needle tip protectors are disclosed in U.S. Pat. No. 4,978,344, U.S. Pat. No. 5,051,109, and U.S. Pat. No. 5,176,655, but all of these suffer from one or more of the disadvantages referred to above.

It is an object of the invention to provide a catheter placement unit with a needle tip protector which reliably prevents needle stick injuries on withdrawal of the needle without requiting the provision of a strap acting between the needle hub and the needle tip protector.

SUMMARY OF THE INVENTION

According to the present invention there is provided a catheter placement unit as defined in the accompanying claims.

The claimed arrangement is advantageous in that it ensures that there can be no accidental separation of the catheter from the unit in such a manner as to expose the contaminated needle tip after the catheter has been placed in position in the patient's body but prior to withdrawal of the needle in the required manner to trigger the shielding action. Furthermore, because the provision of the locking device renders a retaining strap extending between the needle tip protector and the needle hub unnecessary, the same needle tip protector may be used with needles of different lengths, and there is no need for different arrangements to be produced for different needle lengths. The unit may also be produced and assembled relatively easily.

BRIEF DESCRIPTION OF THE DRAWINGS

In order that the invention may be more fully understood, embodiments of catheter placement unit in accordance with the invention will now be described, by way of example, with reference to the accompanying drawings in which:

FIGS. 1 and 2 are broken away top views of a first embodiment in its unlocked and locked positions respectively;

FIG. 3 is a top view of a variant of the first embodiment;

FIGS. 4 and 5 are broken away top views of a second embodiment in its unlocked and locked positions respectively;

FIGS. 6 and 7 are broken away top views of a third embodiment in its unlocked and locked positions respectively; and FIG. 7A is a rear view of part of the third embodiment taken in the direction of the arrow A in FIG. 7.

DETAILED DESCRIPTION OF THE DRAWINGS

The catheter placement unit 1 shown in FIG. 1 comprises an introducing needle 2 mounted on a transparent plastics needle hub 3 in conventional manner, and a flexible tubular catheter 4 mounted on a plastics catheter hub 5 in conventional manner. The needle 2 extends within the catheter bore so that its pointed tip projects from the end of the catheter 4. An annular flange 6 is provided on the end of the catheter hub 5.

In addition the catheter placement unit 1 includes a needle tip protector 8 mounted on the needle 2 between the needle hub 3 and the catheter hub 5. The needle tip protector 8 includes a locking device 9 comprising two co-operating locking parts 10 and 11 which are pivotally interconnected by a pivot post 12 on the part 10 which is a snap fit within a pivot tube 13 on the part 11. It should be appreciated that a top wall of the locking part 11 is shown removed in the FIG. in order to render the interior of the locking device 9 visible, although the opposite wall 14 of the locking part 10 can readily be seen.

The locking part 10 has an end wall 15 provided with a slot 16 through which the needle 2 extends, and the locking part I 1 has an opposite end wall 17 provided with a slot 18 through which the needle 2 also extends in the initial position shown in FIG. 1. The locking part 11 additionally has two side walls 19 and 20. A locking cam 21 is connected to the side wall 19 of the part 11 by a flexible hinge portion 22 so as to permit limited pivotal movement of the locking cam 21 relative to the remainder of the part 11.

The locking parts 10 and 11 also have respective retaining jaws 23 and 24 for retaining the catheter hub 5 therebetween. When the locking device 9 is in the unlocked position, shown in FIG. 1, in which the device is placed during assembly with the needle 2 extending through the slots 16 and 18 in the locking parts 10 and 11, the jaws 23 and 24 firmly engage the catheter hub 5 so as to prevent the catheter 4 being removed from the unit in such a manner as to leave the needle tip exposed after it has been introduced into the patient's body. It will be appreciated that the jaws 23 and 24 are held in this closed position by virtue of engagement of the needle 2 within the two slots 16 and 18. Furthermore, in this unlocked position, the needle 2 holds a tongue 25 on the part 10 in a depressed position in which it compresses a leaf spring 26 located between the tongue 25 and the adjacent side wall 20 of the part 11. In this unlocked position the locking cam 21 is clear of the needle 2 so that the needle may slide in relation to locking device 9 as it is withdrawn from the catheter 4.

In use of the unit to place a catheter in a patient's body, a protective sheath 27 (see FIG. 3) is first removed from the unit, and the tip of the needle 2 is then caused to puncture the patient's skin. The needle hub 3 is then manipulated to place the needle tip in the required position as indicated by the presence of blood in the needle hub 3. When the correct position is reached, the catheter 4 is threaded along the needle by applying pressure with one finger to the ribbed outer surface 28 (see FIG. 3) of the locking part 11. The needle 2 is then slowly withdrawn from the catheter bore by gasping the needle hub 3 with one hand whilst holding the catheter hub with the other hand. When the needle hub 3 has been moved to a sufficient extent to withdraw the needle tip from both the catheter hub 5 and the slot 18 in the locking part 11, the resilient action of the leaf spring 26 causes pivoting of the locking parts 10 and 11 to the locking position shown in FIG. 2, thus releasing the catheter hub 5 by movement apart of the jaws 23 and 24 and permitting separation of the unit from the catheter 4 which remains attached to the patient.

The resilient action of the leaf spring 26 also causes movement of the tongue 25 on the locking part 10 relative to the locking part 11 so as to cause the end of the tongue 25 to override a retaining rib 29 on the end wall 17 of the locking part 11 with the result that the tongue 25 is retained by the rib 29 in a raised position in which it forces the needle 2 into contact with the locking cam 21. The form of the locking cam 21 is such that further withdrawal of the needle 2 from the locking device 9 will cause the locking cam 21 to be pivoted in a clockwise direction as shown by the arrow 30 in FIG. 2 so as to provide increased gripping of the needle 2 by the locking cam 21, with the result that the locking cam 21 provides considerable resistance to withdrawal of the needle 2 from the needle tip protector 8.

Thus the needle tip protector 8 is locked on the end of the needle 2 in such a manner as to safely and reliably shield the needle tip, and the needle 2 may be safely disposed of with the attached protector 8. Since the action of withdrawing the needle tip into the protector 8 simultaneously releases the catheter 4 from the unit, there is no danger of the catheter being accidentally withdrawn from the patient along with the needle or of the protector being pulled off the end of the needle by the catheter.

FIG. 3 shows a variant 1' of the embodiment described in which the only difference is in the form of the needle hub 3' which is provided with integral side walls 31 and 32 which overlap the corresponding side walls of the locking parts 10 and 11 of the needle tip protector 8 and are provided with external gripping surfaces 33 and 34 The gripping surfaces 33 and 34 may be grasped in the vicinity of the needle tip protector 8 between the thumb and finger of the hand in order to hold the needle hub 3 and the needle tip protector 8 together as the needle tip is introduced into the patient's body. The user may then thread the catheter along the needle into the patient's vein by applying a pushing force to the fibbed surface 28 of the needle tip protector 8 with one finger. However the fact that the side walls 31 and 32 overlap the corresponding side walls of the needle tip protector 8 will discourage the user from grasping the needle tip protector 8 during withdrawal of the needle from the catheter bore which might otherwise have the effect of separating the needle tip protector 8 from the needle and exposing the contaminated needle tip.

FIGS. 4 and 5 show a catheter placement unit 40 in accordance with a second embodiment of the invention, like parts being denoted by the same reference numerals as in FIGS. 1 and 2 and the unit 40 being shown respectively in the unlocked and locked positions in FIGS. 4 and 5. In this case the needle tip protector 41 includes a locking device having two locking parts 42 and 43 interconnected by a link 44 provided with a slot 45 through which the needle 2 extends, each of the locking parts 42 and 43 being capable of limited pivotal movement relative to the link 44. Each of the locking parts 42 and 43 is also provided with an integral wall 46 or 47 provided with a slot 48 or 49 through which the needle 2 extends in the unlocked position.

When the needle 2 is withdrawn from the catheter hub 5 and from the slot 49 in the wall 47, this permits retaining jaws 50 and 51 to be sprung apart by a leaf spring 52 in order to release the catheter hub 5, and at the same time results in locking earns 53 and 54 on the locking parts 42 and 43 being brought into forcible engagement with the needle 2 so as to grip the needle 2 therebetween. Such gripping action will tend to be increased by any force applied to the needle 2 in a direction so as to tend to further withdraw the needle.

FIGS. 6 and 7 show a catheter placement unit 60 in accordance with a third embodiment of the invention in the unlocked and locked positions respectively, like parts being denoted by the same reference numerals as in FIG. 1 and 2. In this case the needle tip protector 61 comprises a locking device 62 having a locking part 63 which is slidably attached to the needle 2 and a locking part 64 which is pivotally mounted on the locking part 63 by virtue of an integral cam 65 located between the needle 2 and a curved wall 66 on the locking part 63. In the unlocked position shown in FIG. 6, the locking part 64 is cocked against the action of a torsion spring 67 so that the catheter hub 5 is held in position on the needle 2 by engagement of the catheter hub 5 by the tip 69 of the locking part 64. In this position the cam 65 permits sliding of the needle 2 relative to the locking device 62.

On withdrawal of the needle from the catheter hub 5, the catheter hub 5 is permitted to fall away from the needle tip protector 61 and the locking part 64 is pivoted by the action of the torsion spring 67 into the position shown in FIG. 7 in which it shields the needle tip. Furthermore, because the cam 65 is of slightly oval form, such pivotal movement of the locking part 64 results in gripping of the needle 2 by the cam 65, as shown in the view of FIG. 7A taken in the direction of the arrow A in FIG. 7, and such gripping will be increased by any movement of the needle 2 in the direction tending to withdraw the needle from the needle tip protector 61.

What is claimed is:

1. A catheter placement unit comprising a catheter having an axial bore, a catheter hub at one end of the catheter, an introducing needle having a pointed tip for introducing the catheter into a desired position in a patient's body, a needle hub on the needle remote from the tip for mounting the needle so that it extends through the catheter bore for introduction of the catheter into the patient's body and so that it can subsequently be withdrawn from the catheter bore leaving the catheter in position in the patient's body, and a needle tip protector on the needle for shielding the needle tip when the needle has been withdrawn from the catheter bore, the needle tip protector including a locking device which is initially in an unlocked position permitting withdrawal of the needle from the catheter bore but which is arranged to be placed in a locked position, in which the locking device engages the outer surface of the needle, by withdrawal of the needle from the catheter bore so as to lock the needle tip protector on the needle in the shielding position, and in which the locking device comprises two co-operating locking parts which are pivotally interconnected and have opposing gripping portions thereon and which define a passage through which the needle extends to retain the locking device in the unlocked position when the needle is in its initial position extending through the catheter bore, biasing means for effecting relative pivoting of the locking parts when the needle is withdrawn from said passage on withdrawal from the catheter bore so as to cause the needle to be gripped between said opposing gripping portions of said locking parts to place the locking device in the locked position and catheter engagement means on the locking parts for retaining the catheter hub on the needle when the locking device is in the unlocked position and for releasing the catheter hub from the needle by relative pivoting of the locking parts when the locking device is placed in the locked position such that separation of the catheter from the needle is prevented until the needle has been withdrawn from the catheter bore to trigger shielding of the needle tip.

2. The unit according to claim 1, wherein one of the locking parts includes a tongue which is held in a depressed position by the needle when the needle extends through the catheter bore and which is released when the needle is withdrawn from the catheter bore and from said passage in order to permit the tongue to be moved by resilient action into a raised position in which it is retained by engagement with a retaining element and in which the needle is laterally offset from said passage to prevent re-introduction of the needle into the passage.

3. The unit according to claim 1, wherein one of the locking parts includes a locking cam forming one of said gripping portions which grips the needle when the needle is withdrawn from the catheter bore and from said passage and which is deflected by further withdrawal of the needle in such a manner as to provide increasing resistance to withdrawal of the needle from the needle tip protector.

4. The unit according to claim 1, wherein the catheter engagement means comprises retaining jaws for retaining the catheter hub therebetween to prevent separation of the catheter from the needle tip protector when the locking device is in the unlocked position and for releasing the catheter hub by movement apart of the jaws when the locking device is moved into the locked position on withdrawal of the needle from the catheter bore and from said passage.

5. The unit according to claim 1, wherein the needle tip protector is mounted on the needle such that, when the needle tip protector is in its shielding position, there is no interconnection between the needle hub and the needle tip protector other than that provided by the needle itself.

6. The unit according to claim 1, wherein said biasing means comprises a leaf spring acting between the locking parts so as to be compressed when the locking device is held in the unlocked position by engagement of the needle within said passage.

7. The unit according to claim 1, wherein said passage comprises an aperture extending through a transverse wall on one of the locking parts.

8. The unit according to claim 1, wherein one of the locking parts includes an oval locking cam constituting one of said gripping portions which grip the needle when the needle is withdrawn from the catheter bore and from said passage.

9. The unit according to claim 8, wherein the catheter engagement means comprises a retaining arm which engages the catheter hub when the locking device is in the unlocked position and which effects pivoting of the locking cam to grip the needle when the catheter hub is released on withdrawal of the needle from the catheter bore and from said passage.

\* \* \* \* \*